United States Patent
Phoenix et al.

[11] Patent Number: 6,050,816
[45] Date of Patent: Apr. 18, 2000

[54] PLANAR LIGHT BEAM ORIENTATION DEVICE

[75] Inventors: Rodney D. Phoenix, San Antonio; Robert E. Jones, Mission, both of Tex.

[73] Assignee: Board of Regents The University of Texas System, Austin, Tex.

[21] Appl. No.: 09/058,066

[22] Filed: Apr. 9, 1998

[51] Int. Cl.[7] .................................................. A61C 19/055
[52] U.S. Cl. ............................. 433/55; 33/286; 33/290
[58] Field of Search .................................. 433/29, 55, 56, 433/229; 362/259; 33/290, 286, DIG. 21

[56] References Cited

U.S. PATENT DOCUMENTS

| | | | |
|---|---|---|---|
| 4,111,564 | 9/1978 | Trice, Jr. . | |
| 4,830,489 | 5/1989 | Cain et al. . | |
| 4,836,669 | 6/1989 | Teach | 33/290 |
| 4,836,782 | 6/1989 | Gonser | 433/229 |
| 5,078,599 | 1/1992 | Eenboom et al. | 433/29 |
| 5,440,393 | 8/1995 | Wenz | 356/376 |
| 5,446,635 | 8/1995 | Jehn | 362/259 |
| 5,539,990 | 7/1996 | Le | 33/283 |
| 5,566,459 | 10/1996 | Breda | 33/290 |
| 5,588,216 | 12/1996 | Rank et al. | 33/286 |
| 5,616,141 | 4/1997 | Cipolla | 606/15 |
| 5,673,492 | 10/1997 | Williams | 33/286 |
| 5,836,081 | 11/1998 | Orosz, Jr. | 33/290 |

FOREIGN PATENT DOCUMENTS

| | | |
|---|---|---|
| 0 518 572 | 12/1992 | European Pat. Off. . |
| 0 722 699 | 7/1996 | European Pat. Off. . |
| WO 91/03980 | 4/1991 | Germany . |

*Primary Examiner*—Ralph A. Lewis
*Attorney, Agent, or Firm*—Arnold White & Durkee

[57] ABSTRACT

The present invention provides a planar light beam orientation device comprising a light source, a beam disperser, and a housing coupled to the light source and holding the beam disperser. The housing is configured to have a beam aperture configured to project a planar beam of light therefrom. The planar light beam orientation device of the present invention is capable of projecting a 360° planar beam of light. The device is particularly useful in the orienting and reorienting of dental casts in a dental surveyor.

46 Claims, 4 Drawing Sheets

PLANAR LIGHT BEAM ORIENTATION DEVICE

BACKGROUND OF THE INVENTION

1. Field of the Invention

The present invention relates generally to a planar light beam orientation device and more particularly to a planar light beam orientation device capable of projecting a 360° planar beam.

2. Description of the Related Art

In the practice of dentistry, the making of removable partial dentures is a very exacting process. Careful planning on the part of the dentist is required prior to making the partial denture so that optimum fit and comfort are achieved for the patient.

This planning process requires a careful analysis of models of the patient's teeth, also known as dental casts. This analysis is performed on a device known as a dental surveyor. A dental surveyor is comprised of a horizontal platform to which a vertical arm is affixed. At the top of the vertical arm is an arm projecting horizontally over the surveying platform. This horizontal arm extends to the midpoint of the surveying platform. At the free end of the horizontal arm is a receptacle adapted for receiving a movable downward extending arm. The movable downward extending arm extends vertically towards the surface of the surveying platform and is adapted at its inferior end, i.e., the end projecting towards the surveying platform, to receive various attachments, including a marking stylus. A dental surveyor is also comprised of a surveying table on which a dental cast may be mounted.

The surveying table is adapted so that the surface to which the dental cast is mounted can be reversibly positioned in a given orientation. The surveying table allows for the surface to which the cast is mounted to be tilted in three planes until the optimal orientation is achieved. The cast is then immobilized in that chosen position.

The downward extending arm of the surveyor is positioned so that the marking end of the stylus is in an appropriate horizontal plane with the mounted cast. The stylus is then used to mark the mounted cast in at least three positions. This procedure of marking of the cast is known as tripodization of the cast. The marks on the dental cast all lie in the same horizontal plane which is likewise parallel to the surveying platform. These marks are unique to the marked cast and will be used for subsequent reorientation of the cast and the surveying table in relation to the surveying platform.

A dentist may have dental casts for a number of patients that he may wish to survey for removable partial dentures or for other procedures. Moreover, he may need to remount and reorient a dental cast to re-evaluate a design or for other reasons. Accordingly, the ability to accurately reorient previously evaluated casts is imperative.

Presently, reorienting a previously evaluated dental cast is very much a trial and error process. That is, the dentist or technician must, through continual tilting adjustments of the surveying table, attempt to orient the surface of the surveying table holding the cast so that the horizontal plane created by the stylus marks on the cast is again parallel to the surveying platform. Accordingly, the stylus is moved vertically until the stylus contacts a single mark on the dental cast and then the surveying table holding the dental cast is tilted or adjusted until the other two markings are brought into the same plane. This is a frustrating and time consuming procedure.

Accordingly, a need exists for an apparatus and method making orienting and reorienting dental casts in relation to a dental surveyor easier and more efficient. The present invention meets that need.

SUMMARY OF THE INVENTION

The present invention provides in one aspect, a planar light beam orientation device including a light source; a beam disperser; and a housing coupled to the light source. The housing is adapted to hold the beam disperser. In addition, the housing is configured to include a beam aperture configured to produce a planar beam of light therefrom.

The planar light beam orientation device of the present invention utilizes a high intensity light source, for example, a laser which emits a precise beam of light. The beam disperser has at least one reflective surface and is positioned within the housing so that the reflective surface preferably is oriented at a 45° angle to the incident ray of a beam of light emitted from the light source. Thus positioned, the beam disperser projects a beam of light at a 90° angle to the incident ray of the beam of light emitted from the light source. The beam aperture in the housing defines the projected beam of light so that a planar beam of light is projected from the housing.

In accordance with another aspect of the present invention, a method of orienting a dental cast in a dental surveyor using a planar light beam orientation device is provided. The steps of the method include: mounting a dental cast in a dental surveying table; orienting the dental cast in a desired horizontal plane; attaching a planar light beam orientation device to the movable vertical arm of the dental surveyor and activating the orientation device; positioning the orientation device in a preferred horizontal plane intersecting the dental cast; projecting a horizontal planar beam of light from the orientation device onto the dental cast in the preferred horizontal plane; and marking the dental cast in at least three locations lying in the projected horizontal planar beam of light.

In accordance with another aspect of the present invention, a method of orienting a dental cast bearing orientation marks in a dental surveyor using a planar light beam orientation device is provided. The steps of the method include: mounting a dental cast bearing orientation marks in a dental surveying table; attaching a planar light beam orientation device to the movable vertical arm of the dental surveyor and activating the orientation device; positioning the orientation device in a preferred horizontal plane intersecting the dental cast; projecting a horizontal planar beam of light from the orientation device onto the dental cast in the preferred horizontal plane; and adjusting the dental surveying table so that the orientation marks lie in the projected horizontal planar beam of light.

In another aspect of the present invention, a method of positioning an object in a specific planar position within a confined space using a planar light beam orientation device is provided. The steps of the method include: determining a specific planar position within the confined space for the object; activating the orientation device; positioning the activated orientation device within the confined space in a plane corresponding to the determined specific planar position; projecting a planar beam of light from the orientation device onto at least one surface of the confined space, the plane of the projected beam corresponding to the determined specific planar position; and positioning the object within the confined space in proper relationship to the projected planar beam of light.

In accordance with another aspect of the invention, a dental surveyor is provided. The dental surveyor includes a planar light beam orientation apparatus, a gimballed platform for supporting a dental cast, and a support apparatus for supporting the planar light beam orientation apparatus in a desired orientation with respect to the platform.

The planar light beam orientation apparatus in accordance with the dental surveyor embodiment of the invention includes a light source; a beam disperser; and a housing coupled to the light source, the housing adapted to hold the beam disperser and configured to have a beam aperture configured to produce a planar beam of light therefrom.

The gimballed platform is useful for mounting a dental cast and for orienting the cast in spatial relationship to the planar light beam orientation apparatus. A surveying table is an example of such a gimballed platform. The support apparatus acts to support or hold the planar light beam orientation apparatus in a desired spatial relationship and orientation with the gimballed platform.

BRIEF DESCRIPTION OF THE DRAWINGS

The foregoing and other advantages of the invention will become apparent upon reading the following detailed description and upon reference to the drawings in which.

DETAILED DESCRIPTION OF SPECIFIC EMBODIMENTS

Figure 1:
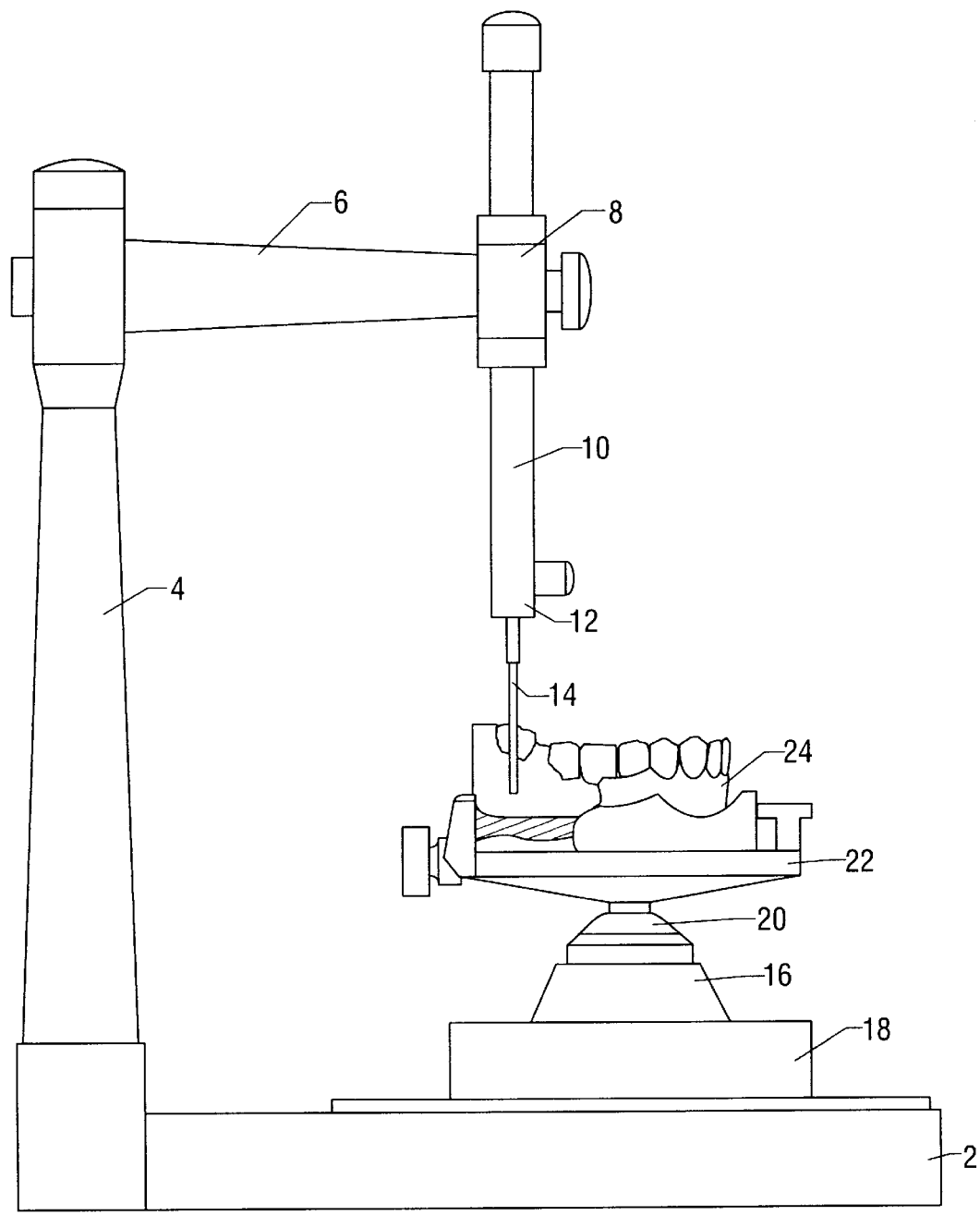
FIG. 1 is a side view of a prior art dental surveyor with a dental cast, shown with a portion broken away, mounted on the surveying table.

FIG. 1 illustrates a dental surveyor of the prior art. The dental surveyor illustrated in FIG. 1 includes a horizontal surveying platform 2 to which a vertical arm 4 is affixed. At the top of the vertical arm is an arm 6 projecting horizontally over the surveying platform. This horizontal arm 6 extends to the midpoint of the surveying platform 2. At the free end of the horizontal arm 6 is a receptacle 8 adapted for receiving a movable downward extending arm 10. The movable downward extending arm 10 extends vertically towards the surface of the surveying platform 2 and is adapted at its inferior end 12, i.e., the end projecting towards the surveying platform 2, to receive various attachments, including a marking stylus 14.

The surveying table 16 includes a base 18, a gimbal 20, and a platform 22 on which the dental cast 24 is mounted. Because of the inclusion of gimbal 20, platform 22 to which the dental cast 24 is mounted can be reversibly positioned in a given orientation. Gimbal 20 may be reversibly loosened by means of a set screw (not shown). When loosened, platform 22 may be tilted in three planes until its optimal orientation is achieved. The set screw is then tightened and platform 22, on which dental cast 24 is mounted, is immobilized in the chosen position.

Figure 2:
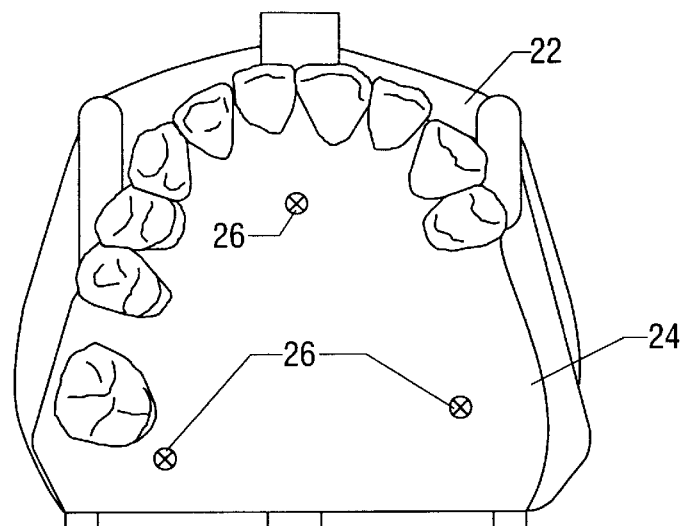
FIG. 2 is a top view of a dental cast mounted on a surveying table, as in FIG. 1, and bearing three orientation marks.

The downward extending arm 10 of the surveyor is positioned so that the marking end of stylus 14 is in an appropriate horizontal plane with mounted cast 24. The stylus 14 is then used to mark mounted cast 24 in at least three positions as can best be seen in FIG. 2. The orientation marks 26 on dental cast 24, as illustrated in FIG. 2, all lie in the same horizontal plane which is likewise parallel to surveying platform 2.

Figure 3:
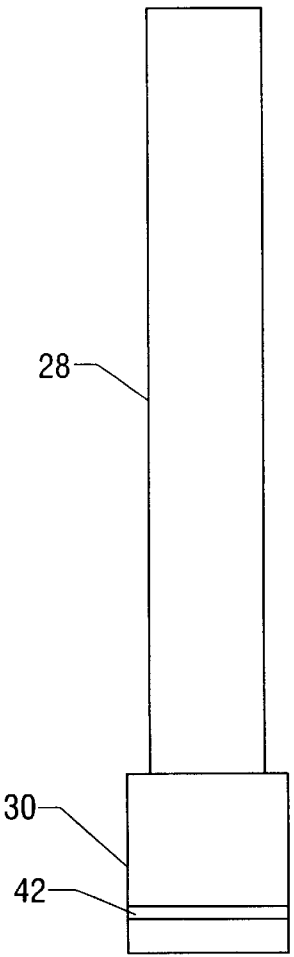
FIG. 3 is a side view of a preferred embodiment of the planar light beam orientation device.
Figure 4:
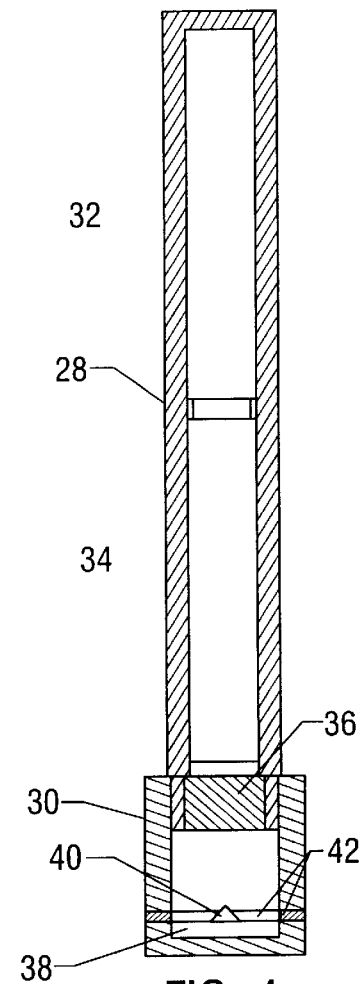
FIG. 4 is a cross-sectional view of the embodiment of the planar light beam orientation device shown in FIG. 3.

FIGS. 3 and 4 illustrate a preferred embodiment of the present invention. The planar light beam orientation device of the present invention as seen in FIG. 3 includes a laser 28 and a housing 30. As seen in FIG. 4, the housing 30 is threaded onto the light emitting end of the laser 28. The laser illustrated in FIGS. 3 and 4 is a low power laser, for example, a laser pointer. In this embodiment, the laser is battery powered as can be more readily determined in FIG. 4. Laser 28 includes a power source, or battery 32, a laser device 34, and a lens 36. Laser device 28 is threaded at its light emitting end, i.e., the end possessing lens 36.

Housing 30 is reciprocally threaded at its open end. While in this preferred embodiment of the present invention, housing 30 is coupled to laser 28 by reciprocal threading, those skilled in the art will appreciate that the housing could be coupled to the laser in any number of ways, e.g., by means of a frictional fit of the housing to the laser.

Retained inside housing 30 is a beam disperser 38. The beam disperser has a reflecting surface 40 which is configured in the shape of a cone whereby its reflecting surface 40 is at a 45° angle to the incident ray of a beam of light emitted from laser 28. This configuration of beam disperser 38 disperses the beam in a planar fashion.

Housing 30 is configured to contain a beam aperture 42 which in this preferred embodiment extends circumferentially about housing 30 and produces a 360° planar beam of light. The width of the beam aperture 42 is configured so as to produce a precise planar beam of light. For the purposes of the present invention, the width of the beam aperture is not critical. Rather, the width of the beam aperture is a matter of choice for the user. The beam aperture may be a slit opening, or more preferably, the opening could be covered or filled with a solid such as glass or a plastic which is transparent and does not distort the projected planar beam of light.

The embodiment of the invention illustrated in FIGS. 3 and 4 is capable of projecting a 360° planar beam. Those skilled in the art will understand that by changing the configuration of the beam aperture, planar beams of less than 360° can be produced. For example, a beam aperture could be configured that extends only halfway around the circumference of the housing producing a 180° planar beam of light. Likewise, a beam aperture could be configured to emit planar beams of light in arcuate segments. Such adaptations may be important for certain applications.

Figure 5:
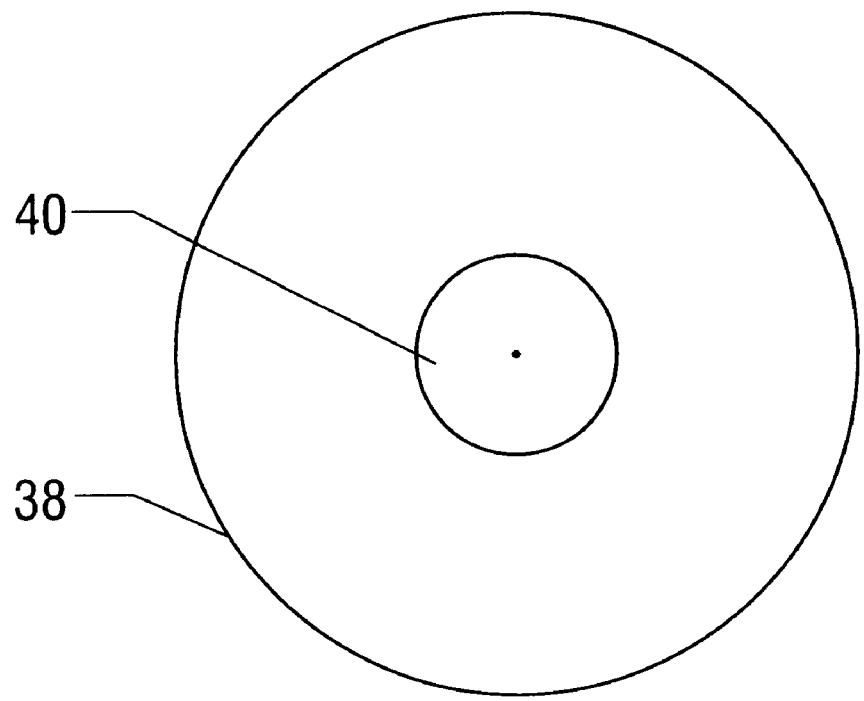
FIG. 5 is a top view of the beam disperser illustrated in FIG. 4.
Figure 6:
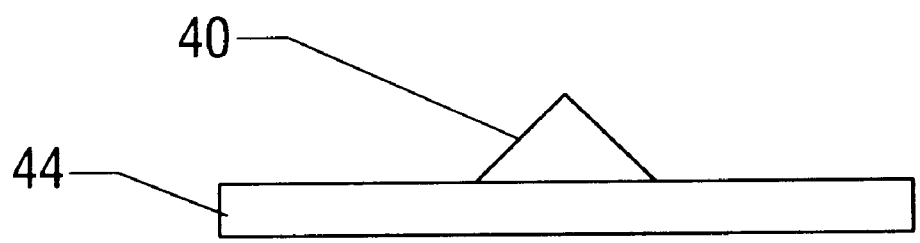
FIG. 6 is a side view of the beam disperser illustrated in FIG. 5.

FIG. 5 illustrates beam disperser 38 from a top perspective. FIG. 6 illustrates beam disperser 38 from a side perspective. Beam disperser 38 includes a reflecting surface 40 and a base 44. Reflecting surface 40 is configured as a reflecting cone so that the reflecting sides of the cone are at a 45° angle to the incident ray of a beam of light projected from laser 28 towards the apex of the cone. Thus, in this preferred embodiment, beam disperser 38 is oriented in housing 30 with the apex of the cone directed towards laser 28. The configuration of reflecting surface 40 disperses the beam emitted from laser 28 at a 90° angle to its incident ray toward beam aperture 42 in a planar fashion.

As envisioned for use in the present invention, the beam disperser should meet certain criteria. The reflecting surface of the beam disperser should be configured so that the incident beam emitted from the light source will be projected from the reflecting surface of the beam disperser in such a manner as to project the desired planar beam of light. Those skilled in the art will appreciate that the reflecting surface may be configured in any number of ways and still project a planar beam of light. For example, the reflective surface may be a flat surface or a curved surface. To project a 360° planar beam of light, the reflecting surface may be a smooth, continuous surface as in the preferred embodiment or may be multi-faceted as in a pyramid. To project less than a 360° planar beam of light, the reflecting surface may be configured as described above but with only the appropriate portions of the reflecting surface made reflective.

The reflecting surface should also possess appropriate optical qualities, e.g., the reflecting surface should be highly reflective and should not alter or otherwise distort the beam of light projected onto its surface. Thus, any material possessing these optical qualities or capable of being treated so as to attain such properties and also capable of being appropriately configured for the purposes of the present invention is a satisfactory material for the manufacture of the reflecting means.

In this preferred embodiment, beam disperser 38 was fabricated of nickel and reflecting surface 40 was sputter coated with rhodium. The entirety of reflecting surface 40, i.e., the entire surface of the cone, was coated with rhodium rendering it reflective. Beam disperser 38, as illustrated in FIGS. 4–6, is approximately 3 mm in height, base 44 comprising approximately 1 mm and reflecting surface 40 comprising the remaining 2 mm. The diameter of the base of reflecting surface 40 is approximately 4 mm which approximates the diameter of the beam projected by laser 28. Beam disperser 38 as illustrated in FIGS. 4–6 was manufactured by Opti-Forms, Inc. of Temecula, Calif.

A laser is particularly preferred for use in the present invention. While the laser primarily serves as a light source for creating the planar beam, the beam of light produced by a laser is well delineated, well defined and intense, producing a visible, precise planar beam. Other light sources may be used, however, these other light sources may be susceptible to scatter and bending of the planar beam thus lacking the intensity and precision of the planar beam created by a laser. Nonetheless, for the purposes of this invention, any high intensity light source capable of providing a well defined, well delineated, non-destructive beam of visible light would be satisfactory.

Figure 7:
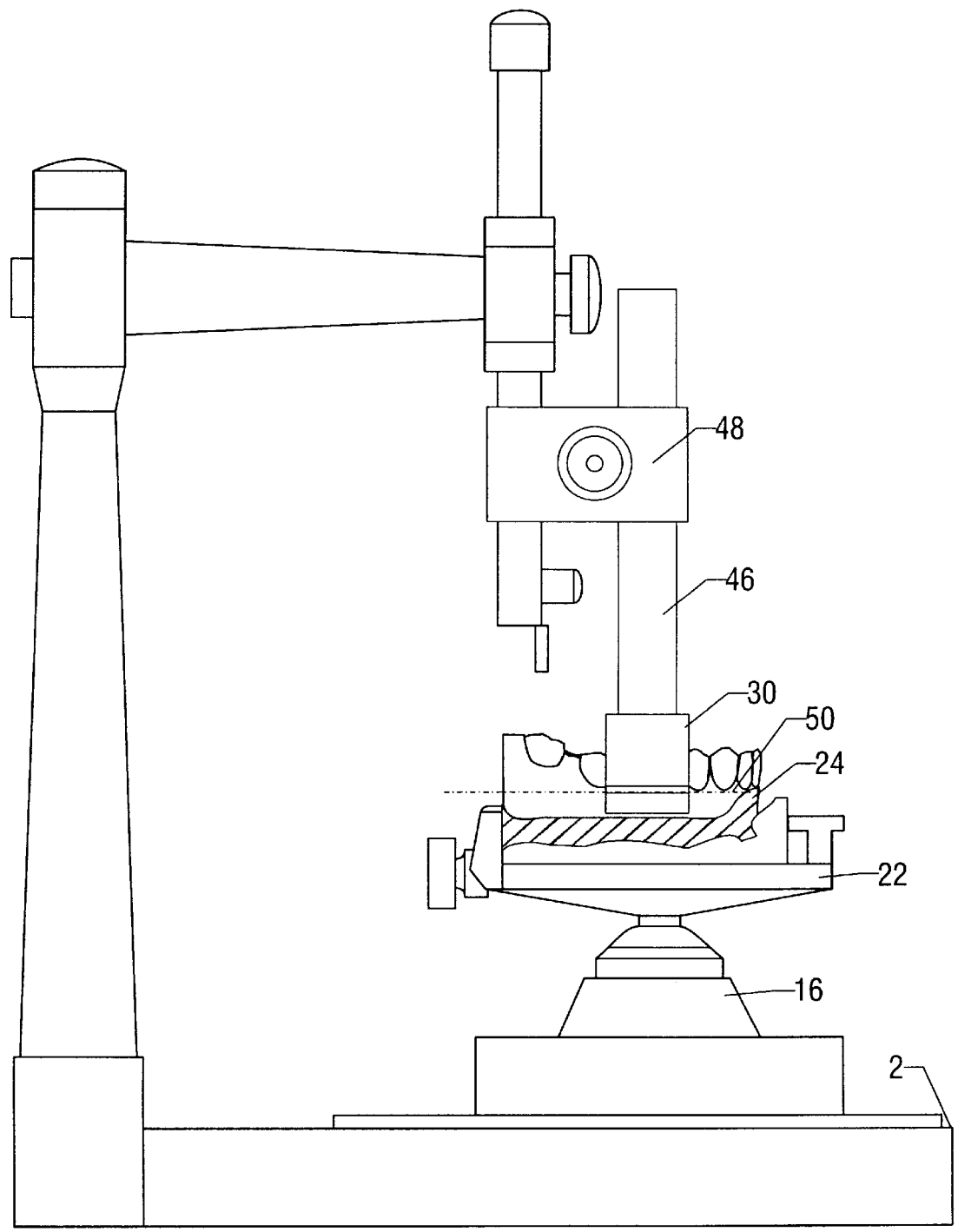
FIG. 7 is a side view of a preferred embodiment of the planar light beam orientation device, as shown in FIG. 3, attached to a dental surveyor and a dental cast, shown in cross-section, mounted on a surveying table.

Referring to FIG. 7, a dental surveyor equipped with the planar light beam orientation device of the present invention may be used to orient a dental cast in the first instance as well as to reorient a previously mounted dental cast. To orient a dental cast, cast 24 would first be mounted on platform 22 of surveying table 16 and platform 22 oriented as desired by the dentist or technician. Planar light beam orientation device 46 would then be attached to vertically extending arm 10 by attachment means 48 so that housing 30 extends downwards vertically towards dental cast 24. Planar light beam orientation device 46 would then be activated, thus projecting a horizontal planar beam of light 50. Vertical arm 10 would then be adjusted to position planar light beam orientation device 46 vertically downward until planar beam 50 intersected with dental cast 24 as desired. The dentist or technician would then mark dental cast 24 in at least three locations in the horizontal plane indicated by planar beam 50 projected onto dental cast 24.

In some instances, it may be desirable to reorient a previously surveyed cast or to orient a cast which bears orientation marks. A master cast on which a removable partial denture is to be fabricated will bear orientation marks transferred by the dentist or technician to the master cast from the surveyed cast. During the fabrication of the removable partial denture, it will be desirable to orient the master cast in a dental surveyor.

To orient a dental cast bearing orientation marks as illustrated in FIG. 2, dental cast 24 would first be mounted on platform 22 of surveying table 16. Platform 22 would then be preliminarily oriented by the dentist or technician in an attempt to place the orientation marks in the same horizontal plane. Planar light beam orientation device 46 would then be attached to vertically extending arm 10 by attachment means 48 so that housing 30 extends downward vertically toward dental cast 24. Planar light beam orientation device 46 would then be activated, thus projecting a horizontal planar beam of light 50. Vertical arm 10 would then be adjusted to position planar light beam orientation device 46 vertically downward until planar beam 50 intersected with the dental cast 24 in the same horizontal plane as the orientation marks. Platform 22 would then be adjusted so that all of the orientation marks on the dental cast lie in the same horizontal plane as planar beam 50 projected onto cast 24.

The planar light beam orientation device of the present invention, while developed for a dental application, has many other potential uses. For example, a properly dimensioned planar light beam orientation device could be used for building and construction purposes to provide a precise level across a planar surface. Likewise, such a device could be used for precise placement of a component, module, or some similar object in a confined space, particularly in cylindrical environments. A planar light beam orientation device of the present invention could also be used as a fluid level indicator, for example, in a tank. A planar light beam orientation device of the present invention could also have security applications, for example providing a planar security beam that if breached would trigger an alarm. These suggested uses for the present invention are not meant to be inclusive of all possible uses that will be recognized by those skilled in the art.

While the invention may be susceptible to various modifications and alternative forms, specific embodiments have been shown by way of example in the drawings and have been described in detail herein. However, it should be understood that the invention is not intended to be limited to the particular forms disclosed. Rather, the invention is to cover all modifications, equivalents, and alternatives falling within the spirit and scope of the invention as defined by the following appended claims.

What is claimed is:

1. A dental surveyor comprising:
 a planar light beam orientation apparatus, the planar light beam orientation apparatus including a light source; a beam disperser; and a housing, the housing being adapted to hold the beam disperser and the light source and having a beam aperture configured to produce a planar beam of light therefrom, the beam disperser being held by the housing in relationship to the light source so that an incident ray of a beam of light emitted from the light source would be reflected from a surface of the beam disperser to the beam aperture, the beam of light would be collimated by the beam aperture and pass through the beam aperture as a planar beam of light;

an adjustable platform for supporting a dental cast, the platform being useful for orienting the dental cast in spatial relationship to the planar light beam orientation apparatus; and a support apparatus for supporting the planar light beam orientation apparatus in a desired orientation with respect to the platform.

2. The dental surveyor of claim 1 wherein the light source is a laser.

3. The dental surveyor of claim 1 wherein the beam disperser is a reflecting cone, the reflecting cone being spaced apart from the light source and being held by the housing with its apex oriented toward the light source.

4. The dental surveyor of claim 1 wherein the beam disperser has a plurality of reflecting surfaces, each reflecting surface oriented at a 45° angle to an incident ray of the beam of light emitted from the light source.

5. The dental surveyor of claim 1 wherein the beam disperser has at least a single reflecting surface oriented at a 45° angle to an incident ray of the beam of light emitted from the light source.

6. The dental surveyor of claim 1 wherein the beam aperture is configured to produce a 360° planar beam of light.

7. The dental surveyor of claim 1 wherein the beam aperture is configured to produce a plurality of arcuate planar beams of light.

8. The dental surveyor of claim 1 wherein the gimballed platform is a surveying table.

9. A method of orienting a dental cast in a dental surveyor using a planar light beam orientation device comprising the steps of:

mounting a dental cast on a dental surveying table;

orienting the dental cast in a desired horizontal plane;

coupling a planar light beam orientation device to a movable vertical arm of the dental surveyor and activating the orientation device;

positioning the orientation device in a horizontal plane intersecting the dental cast;

projecting a horizontal planar beam of light from the orientation device onto the dental cast; and marking the dental cast in at least three locations lying in the projected horizontal planar beam of light.

10. A method of orienting a dental cast bearing orientation marks in a dental surveyor using a planar light beam orientation device comprising the steps of:

mounting the dental cast bearing orientation marks in a dental surveying table;

affixing a planar light beam orientation device to a movable vertical arm of the dental surveyor and activating the orientation device;

positioning the orientation device in a horizontal plane intersecting the dental cast;

projecting a horizontal planar beam of light from the orientation device onto the dental cast; and adjusting the dental surveying table so that the orientation marks lie in the projected horizontal planar beam of light.

11. The method of claims 9 or 10 wherein the planar light beam orientation device is configured to produce a 360° planar beam of light.

12. The method of claims 9 or 10 wherein the planar light beam orientation device is configured to produce a plurality of arcuate planar beams of light.

13. A method of orienting a dental cast in a dental surveyor using a planar light beam orientation device comprising the steps of:

mounting a dental cast on an adjustable cast holding device;

orienting the dental cast in a desired plane;

positioning a planar light beam orientation device which is coupled to an arm of the dental surveyor relative to the dental cast;

projecting a planar beam of light from the orientation device onto the dental cast; and noting a plurality of locations on the dental cast where the planar beam of light contacts the dental cast.

14. The method of claim 13 further comprising the step of marking the locations on the dental cast where the planar beam of light contacts the cast.

15. The method of claim 13 wherein the adjustable cast holding device is a gimbaled platform.

16. The method of claim 13 wherein the adjustable cast holding device is a dental surveying table.

17. The method of claim 13 wherein the arm of the dental surveyor is movable.

18. The method of claim 13 wherein the desired plane is the horizontal plane.

19. The method of claim 13 wherein the desired plane is the vertical plane.

20. The method of claim 13 wherein the planar light beam orientation device is configured to produce a 360° planar beam of light.

21. The method of claim 13 wherein the planar light beam orientation device is configured to produce a plurality of arcuate planar beams of light.

22. A method of orienting a dental cast bearing orientation marks in a dental surveyor using a planar light beam orientation device comprising the steps of:

mounting the dental cast bearing orientation marks in an adjustable cast holding device;

positioning a planar light beam orientation device which is coupled to an arm of the dental surveyor relative to the dental cast;

projecting a planar beam of light from the orientation device onto the dental cast; and adjusting the cast holding device so that the orientation marks lie in the projected planar beam of light.

23. The method of claim 22 wherein the adjustable cast holding device is a gimbaled platform.

24. The method of claim 22 wherein the adjustable cast holding device is a dental surveying table.

25. The method of claim 22 wherein the arm of the dental surveyor is movable.

26. The method of claim 22 wherein the desired plane is the horizontal plane.

27. The method of claim 22 wherein the desired plane is the vertical plane.

28. The method of claim 22 wherein the planar light beam orientation device is configured to produce a 360° planar beam of light.

29. The method of claim 22 wherein the planar light beam orientation device is configured to produce a plurality of arcuate planar beams of light.

30. A method of orienting a dental cast in a dental surveyor using a planar light beam orientation device comprising the steps of:

mounting a dental cast on an adjustable cast holding device;

orienting the dental cast in a desired plane;

positioning the dental cast relative to a planar light beam orientation device which is coupled to an arm of the dental surveyor;

projecting a planar beam of light from the orientation device onto the dental cast; and noting a plurality of locations on the dental cast where the planar beam of light contacts the dental cast.

31. The method of claim 30 further comprising the step of marking the locations on the dental cast where the planar beam of light contacts the cast.

32. The method of claim 30 wherein the adjustable cast holding device is a gimbaled platform.

33. The method of claim 30 wherein the adjustable cast holding device is a dental surveying table.

34. The method of claim 30 wherein the arm of the dental surveyor is movable.

35. The method of claim 30 wherein the desired plane is the horizontal plane.

36. The method of claim 30 wherein the desired plane is the vertical plane.

37. The method of claim 30 wherein the planar light beam orientation device is configured to produce a 360° planar beam of light.

38. The method of claim 30 wherein the planar light beam orientation device is configured to produce a plurality of arcuate planar beams of light.

39. A method of orienting a dental cast bearing orientation marks in a dental surveyor using a planar light beam orientation device comprising the steps of:

mounting the dental cast bearing orientation marks in an adjustable cast holding device;

positioning the dental cast relative to a planar light beam orientation device which is coupled to an arm of the dental surveyor;

projecting a planar beam of light from the orientation device onto the dental cast; and adjusting the cast holding device so that the orientation marks lie in the projected planar beam of light.

40. The method of claim 39 wherein the adjustable cast holding device is a gimbaled platform.

41. The method of claim 39 wherein the adjustable cast holding device is a dental surveying table.

42. The method of claim 39 wherein the arm of the dental surveyor is movable.

43. The method of claim 39 wherein the desired plane is the horizontal plane.

44. The method of claim 39 wherein the desired plane is the vertical plane.

45. The method of claim 39 wherein the planar light beam orientation device is configured to produce a 360° planar beam of light.

46. The method of claim 39 wherein the planar light beam orientation device is configured to produce a plurality of arcuate planar beams of light.

* * * * *